(12) United States Patent
Moy (10) Patent No.: US 9,669,045 B2
(45) Date of Patent: *Jun. 6, 2017

(54) TREATMENTS FOR ACTINIC KERATOSES (71) Applicant: Lawrence Moy, Manhattan Beach, CA (US)

(72) Inventor: Lawrence Moy, Manhattan Beach, CA (US)

(73) Assignee: Lawrence Moy, Manhattan Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,860

(22) Filed: May 23, 2014

(65) Prior Publication Data

US 2014/0256667 A1 Sep. 11, 2014

Related U.S. Application Data

(63) Continuation of application No. 13/462,681, filed on May 2, 2012, now Pat. No. 8,741,857.

(60) Provisional application No. 61/592,532, filed on Jan. 30, 2012.

(51) Int. Cl.
*A61K 31/7036* (2006.01)
*A61K 31/165* (2006.01)
*A61K 9/06* (2006.01)

(52) U.S. Cl.
CPC ............ *A61K 31/7036* (2013.01); *A61K 9/06* (2013.01); *A61K 31/165* (2013.01)

(58) Field of Classification Search
CPC .......................... A61K 31/7036; A61K 31/165
See application file for complete search history.

(56) References Cited

U.S. PATENT DOCUMENTS

2006/0286108 A1* 12/2006 Bell ..................... A61K 31/635
424/145.1

OTHER PUBLICATIONS

Akar et al, "Efficacy and safety assessment of 0.5% and 1% colchicine cream in the treatment of actinic keratoses", Journal of Dermatological Treatment (2001), vol. 12, pp. 199-203.*
Levender et al., J. Am. Acad. Dermatol., 2012, 66(3), p. 445-451.e3, Available online Aug. 6, 2011.*

* cited by examiner

*Primary Examiner* — Jonathan S Lau
(74) *Attorney, Agent, or Firm* — Stefan J. Kirchanski; Zuber Lawler & Del Duca LLP (57) ABSTRACT

A composition of gentamicin and colchicine in a dermatologically acceptable cream base provided improved clearance of actinic keratoses following topical application for 1 to 3 months. The composition provides improved clearance of recalcitrant actinic keratoses. Furthermore, the treatment causes less pain and irritation than other topical treatments for actinic keratoses.

11 Claims, 6 Drawing Sheets

TREATMENTS FOR ACTINIC KERATOSES

This application is a continuation-in-part of U.S. patent application Ser. No. 13/462,681, now U.S. Pat. No. 8,741,857, which application claims priority from and the benefit of U.S. Provisional Patent Application No. 61/592,532 filed 30 Jan. 2012.

AREA OF THE ART

The present invention is in the art of dermatology and more specifically relates to a topical composition for the treatment of actinic keratoses.

DESCRIPTION OF THE BACKGROUND OF THE INVENTION

Not too long ago most people in the United States and Europe generally avoided excessive exposure to sunlight. Males wore hats that usually included brims large enough to substantially shade the face and neck. At least in the upper and middle classes the typical male garb rarely exposed significant regions of bare skin. Even bathing suits would often cover substantial portions of the male torso including arms and legs—bare chests were unheard of. Females were even more sun protected. Ladies wore large hats complete with veils and scarves. Use of a parasol when outdoors was de rigueur. Female costumes provided even more coverage than male costumes. Until the 1920's even exposed ankles were often considered scandalous. A great premium was placed on delicate white female complexions without any tan or freckling or symptoms of sun exposure.

But the attitude to sun exposure has changed dramatically in the last 50 years or so. First the restrictions on exposure of the male torso were gradually relaxed. Bare arms and legs and even bare chests became acceptable. Today in the western world only coverage of the male genitalia is enforced. At the same time a tan was reevaluated from being a sign of a member of the lower classes to being a sign of vigor and health. A similar but less dramatic transformation also affected the female costume. Bare arms, legs and stomachs became acceptable. Only the female genitalia and to a lesser extent the female bosom remain concealed. It is now considered attractive for females to be tanned and show other symptoms of sun exposure.

Although some exposure to sun light is critical to the synthesis of Vitamin D, sun light is not harmless. Absorption of infra-red light results in heating of the skin and can potentially damage tissues through a "cooking-like" phenomenon. Absorption of visible and ultra-violet light also causes heating, but these wavelengths are much more energetic. Ultra-violet light, and to a lesser extent visible light, are sufficiently energetic to result in chemical changes. The tanning response is largely the skin's attempt to protect itself by providing a shading barrier to sunlight. Although light can induce chemical changes (i.e., damage) to a large variety of biological structures, probably the most significant damage is caused by the ability of ultra-violet light to induce photochemical changes in the pyrimidine bases of DNA (deoxyribonucleic acid). A common expression of this photochemistry is the dimerization of the thymine bases. Such dimerization affects the replication and translation of the genetic material. Cells contain repair mechanisms to excise and replace the damaged regions of DNA, but these mechanisms are not one hundred percent accurate. Therefore, ultra-violet damage introduces mutations into the DNA which can result in abnormal cell growth including precancerous and cancerous lesions.

A common ultra-violet induced lesion occurs when the genetic material of the keratinocytes becomes damaged. Specifically, DNA alterations of keratinocytes in the basal layer of the epidermis result in Actinic Keratoses (AKs). The AKs are crusty, thick, scaly and/or often pigmented premalignant (precancerous) lesions. When abnormal cells spread to or occur in the dermis, the lesion is defined as a squamous cell carcinoma, and the lesion has converted into a true skin cancer. Because a significant number of AKs progress to squamous cell carcinoma, it is important to treat (i.e., remove) AKs. The treatment of Actinic Keratoses (AKs) is very common in dermatology particularly in sunny regions. Increased sun activities over a lifetime increase the risk for these AK's. In Southern California, AKs are very prevalent in the population from the age of 30 years to the elderly.

At the present time, the conventional treatment for AKs is to spray or apply cryogenic liquid nitrogen ($LN_2$) to the lesions. This treatment generally works well for discrete specific lesions; however, the skin can experience sufficient sun damage that AKs will keep appearing even with regular liquid nitrogen treatment. There are some creams that can treat incipient AKs and/or AKs that that are already present. The most common creams contain 5-fluorouracil (5% is the most popular concentration), an anticancer medication. The compound is actually an artificial analog of the DNA base thymidine. It is known as a "suicide inhibitor" because it irreversibly blocks the enzyme thymidylate synthase. Blocking the synthase results in a shortage of thymidine which blocks DNA replication in rapidly growing cancer and precancerous cells thereby resulting in cell death. The reaction to this treatment is typically 4-6 weeks in duration and results in crusted, very painful, very red lesions and peeling of the skin. Even when the 5-fluorouracil treatment is effective, AKs can return and the patient still needs to be followed to watch for further development of AKs.

In my more than 25 years of practicing dermatology, my patients have reported some ultimately positive results from the 5-fluorouracil creams, but most patients would choose not to go through the 4-6 weeks of discomfort and unsightly appearance that results from the treatment.

Current AK treatments are all have significant drawbacks. Liquid nitrogen treatments require regular freezing to the affected areas for adequate control of AKs. $LN_2$ is a common treatment that can be effective in some cases. However, with an increased number of lesions on the face, $LN_2$ treatment can become very traumatic. The freezing hurts and causes scabbing, crusting, blistering and pain for 7-10 days. In addition, it can result in scarring. In some cases, depending on how much sun damage has accumulated over the years or depending on the ongoing sun damage the patient is still receiving (e.g. lifeguards), $LN_2$ treatment is not effective. Furthermore for other body areas, including the scalp or the arms and legs, $LN_2$ treatment is less effective.

The anti-AK creams that are available, notably 5-flourouracil creams, are often very hard on the patient. The treatment results in 4-6 weeks of pain with crusting and scabbing over the entire area of the application, which often includes the entire face. Patients have a very difficult time with the creams if they need to be seen in public for employment purposes or at any social occasion. Many patients who have received 5-flourouracil treatments regret having taken those treatments because of the side effects.

In addition, some patients without obvious onset of squamous cell carcinoma (SCC) or basal cell carcinoma (BCC) show conversion of the AKs to SCC or BCC. With an excessive amount of chronic sun exposure, there is an increase of progression of AKs to skin carcinomas.

Clearly alternate treatments for AKs beyond $LN_2$ and 5-fluorouracil are sorely needed.

SUMMARY OF THE INVENTION

Aminoglycoside antibiotics such as gentamicin have unexpectedly been found to provide an effective treatment for actinic keratoses when applied topically in a dermatologically acceptable cream base. Greatly improved results are achieved by combining gentamicin with tubulin binding drugs such as colchicine in the same cream base. Combinations ranging between 1% and 0.1% by weight of each of these two ingredients have proven to be more effective and less irritating than competing topical treatments. It is believed that alteration of m-RNA translation by the aminoglycoside—particularly correction of Nonsense mutations—combined with the cell division slowing properties of the tubulin binding drug results in either correction of the genetic cause of the lesion or in apoptosis of the altered cells. The combination of an aminoglycoside with a tubulin binding drug offers a new approach to the treatment of actinic keratoses and related precancerous skin conditions.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a novel topical composition for the improved treatment of actinic keratoses.

Ingredients of the Composition

As detailed below the major active ingredients of the composition are colchicine and an aminoglycoside antibiotic (namely gentamicin) in a dermatologically acceptable cream base. The cream base is an oil-in-water emulsion of lipophilic components including caprylic/capric triglycerides, stearyl alcohol, stearic acid and diisopropyl dimer dilinoleate with glyceryl monosterate, PEG-100 Stearate and PEG-40 Stearate as emulsifiers. Propylene glycol is included as a cosolvent. Aluminum magnesium silicate and silica are used as thickening, opacifying agents. Trace amounts of methylparaben, propylparaben, imidazolidinyl urea, propyl gallate and BHA (butylated hydroxyanisole) are added as antioxidants and preservatives. Citric acid is used as a pH adjustor and preservative.

The major active ingredients used in the current invention are generally not available in any commercial product for treatment of precancerous lesions of the skin. This combination of these two active ingredients has never been used for treatment of precancerous or other dermatological conditions. Furthermore, the combination is synergistic resulting in greater effectiveness than either ingredient alone or than would be expected from the combination of the ingredients.

Aminoglycosides.

Aminoglycosides are antibiotics that also show anti-inflammatory effects and suppressive effects on translation of nonsense mutations. Aminoglycoside antibiotics have generally not been available for use as a topical skin product although they are approved for and used as orally administered and intra-venous antibiotics. There are actually a number of rather different antibiotics included in the aminoglycoside group. The antibiotics used in the present invention include aminoglycosides such as gentamicin and tetracycline that exhibit anti-inflammatory effects when applied to the skin. In the late 1960's Dr. Ronald Reisner and Dr. Madeline Puhvel demonstrated that tetracycline antibiotics were anti-inflammatory when used in the treatment of acne. They demonstrated that the anti-inflammatory benefits were not related to the antibacterial properties of the antibiotics.

One of the important properties of the aminoglycoside antibiotics useful in the present invention is their effects on m-RNA translation. Antibiotics are produced by microorganisms as chemical weapons used against competing microorganisms. One site of attack is protein synthesis. Some aminoglycosides bind to ribosomes and distort the interaction between the m-RNA and the ribosome so as to result in the incorporation of incorrect amino acids during protein synthesis. In the wild this distortion of protein synthesis can kill or severely disable a cell. Obviously, these antibiotics do not have this effect on mammalian ribosomes (or else they would never be used therapeutically). However, it turns out that they can have more subtle effects on mammalian protein synthesis.

Nonsense Mutations.

A nonsense mutation is a point mutation in a sequence of DNA that results in the substitution of a STOP codon for a codon specifying an amino acid. When the mutated gene is translated on the ribosome, the STOP codon causes the protein being synthesized to terminate prematurely, often as a non-functional peptide. This differs from a missense mutation, which is a point mutation where a single nucleotide is changed thereby causing substitution of a different amino acid. Some genetic disorders, such as thalassemia and DMD (Duchenne muscular dystrophy), result from nonsense mutations. In the case of a nonsense mutation analysis of the non-functional mutant protein will show that it is shorter than the functional wild type protein.

Nonsense mutations can result in a genetic disease by causing the malfunction of a critical protein; for example, dystrophin in DMD. The same genetic disease may, however, be caused by other kinds of damage to the same gene. Examples of diseases in which nonsense mutations are known to be among the causes include: Cystic fibrosis (caused by mutations in the cystic fibrosis transmembrane conductance regulator (CFTR) gene); DMD (dystrophin); Beta thalassemia (β-globin); and Hurler syndrome (alpha-L-iduronidase)

More recently nonsense mutations have been recognized as possible causes of some cancers. It has long been known that cancers often result from genetic damage. Although the precise reasons for the link between mutations and cancer is not yet know, it is generally hypothesized that mutation can cause cancer by directly damaging genes for cellular systems that suppress cancer. In some cases failure of cellular regulatory mechanisms can result in uncontrolled cell growth. Loss of receptors that lead to cell apoptosis can also result in cancer. A recent study demonstrated the presence of nonsense mutations in squamous cell cancers of the skin. (Kubo, Y. et al., *J Invest Dermatol*. 1994 April; 102(4):440-4.)

Aminoglycosides have found use in blocking nonsense genes. There is an extensive literature on attempts to use these antibiotics to treat some of the genetic diseases listed above. Essentially, by distorting the m-RNA binding site on the ribosome, these antibiotics can cause the STOP codon to be misread so that protein synthesis continues on through the nonsense mutation and the rest of the gene is translated. This will often result in a fully functional or nearly fully functional protein, thereby obviating the genetic disease.

I reasoned that AKs could well be caused by light-induced nonsense mutations which destabilized growth of the cells. If aminoglycosides are able to suppress at least some of these mutations, the abnormal growth patterns of these precancerous lesions might be reversed. Generally such a treatment would be expected to have fewer side effects than toxic agents such as 5-fluorouracil. Alternatively, suppression of some of the mutations might facilitate cellular apoptosis. Either way the AKs would be eliminated.

Colchicine.

Colchicine is an alkaloid that binds to tubulin (the protein makes up microtubules). This binding blocks the polymerization of tubulin into microtubules and inhibits mitosis (cell division) because mitosis is dependent on microtubules to form the spindle, a structure that distributes the chromosomes during cell division. Thus, colchicine can block cell division. For this reason colchicine continues to be investigated as an anticancer drug. At one time colchicine was used as a treatment for skin cancers and precancerous lesions (AKs) of the skin, and colchicine has been studied in the medical literature for AKs over the years, although in the last 17-20 years, there has not been a study that actually used the ingredient.

Gentamicin 1% Cream, Alone.

We studied twenty patients with this formulation applied to AK lesions once a day for either 1 month or 3 months. We instructed the patients to apply the cream to specific skin areas that included dermatologist diagnosed AKs. The results showed that the extent of actinic keratoses decreased by an average of 30% in the twenty patients. Most of the patients applied the cream to the face—a common site for AKs. There were also a number of males who applied the material to sun-exposed areas of the scalp. Additionally, there were some women using it on AKs of the legs.

There was a low level (5-10%) of total improvement or clearing of AKs. Although gentamicin is known to have anti-inflammatory properties, this would not be expected to account for the improvement in the AKs. Most probably the suppression of nonsense mutations allowed genetic repair mechanisms to operate and actually correct some of the underlying genetic damage.

Colchicine 0.1% Cream, Alone.

Testing with colchicine alone, we found that 35-40% of the actinic keratoses were cleared in the patients tested. Unfortunately, this treatment showed a significant level of skin irritation. Skin irritation is likely the reason that colchicine is not commonly used in dermatologic treatments.

Combined 1% Gentamicin and 0.1% Colchicine Cream.

The same study format of once daily application for 1 and 3 months was followed. The cream was exactly the same formulation base as the cream with gentamicin. We have noticed some increased irritation from this product as compared to gentamicin or cream base alone, but the combination is less irritating than colchicine alone. We have had some patients use the combination cream once every other day to reduce irritation. The results were that approximately 60% of the AKs were eliminated after 3 months of use.

Combined 0.3% Gentamicin and 0.2% Colchicine Cream.

Our preliminary experiments suggested that the combination of gentamicin with colchicine reduced the overall irritation caused by colchicine alone. With this in mind we experimented with reducing the percentage of gentamicin to determine whether that would affect the overall level of irritation and/or effectiveness. We also experimented with increasing the percentage of colchicine reasoning that a higher amount might be better tolerated in the presence of gentamicin. The combination of 0.3% gentamicin with 0.2% colchicine appears to provide maximum effectiveness with minimum irritation. Of course, other combinations ranging between 1% and 0.1% gentamicin and 1% and 0.1% colchicine may prove to be particularly effective.

Trial of 0.3% Gentamicin and 0.2% Colchicine Cream.

We gathered difficult patients who were not responding well to $LN_2$ treatment of AKs. Often recalcitrant cases will be males with lesions on the scalp and females with lesions on the legs. Because my practice is located in Manhattan Beach, Calif. we were able to recruit many patients with an average sun exposure much higher than even other regions within the Los Angeles metropolitan area. Patients in Manhattan Beach are typically involved in a number of outdoor-related activities that significantly increase sun exposure. This high level of current sun exposure definitely keeps AK's recurring or failing to resolve. Many of the patients grew up in Manhattan Beach as well so that their overexposure to the sun has been lifelong.

Patients were instructed to apply the inventive cream to the affected areas once per day and were evaluated monthly. Responses were tabulated (Table 1) based on how well the cream worked on the difficult AK's; the overall response, based on the percentage of AK's that were cleared, was also tabulated.

TABLE 1

| Patient | Total response(0/10)[1] | % AK[2] | Gender | Location | Reaction | Patient comment |
|---|---|---|---|---|---|---|
| AA | 6 | 65% | M | Face | — | — |
| BA | 7 | 60% | F | Legs | — | — |
| BL | 6 | 50% | M | Face | — | — |
| CM | 8 | 75% | F | Face | — | — |
| CS | 9 | 75% | M | Face, scalp | — | Great response; should be |

TABLE 1-continued

| Patient | Total response(0/10)[1] | % AK[2] | Gender | Location | Reaction | Patient comment |
|---|---|---|---|---|---|---|
| CT | 8 | 75% | F | Legs | — | patented. No recurring AKs unlike before |
| DG | 8 | 70% | F | Face | — | Good control of difficult area |
| DW | 9 | 100% | M | Face | Redness for 2 weeks. | Cleared area that always recurred |
| HL | 9 | 70% | M | Scalp | — | Scalp has never been better |
| JB | 8 | 80% | M | Legs | — | Works where LN$_2$ does not |
| JC | 5 | 40% | M | Face | — | — |
| KL | 7 | 65% | M | Scalp | — | — |
| LK | 8 | 70% | F | Face | — | Great response. Don't run out |
| MW | 6 | 50% | F | Legs | — | — |
| NK | 4 | 30% | F | Legs | — | — |
| PS | 6 | 60% | F | Face | — | — |
| RA | 8 | 70% | M | Face, back | — | — |
| RH | 7 | 75% | M | Legs | — | — |
| RW | 10 | 90% | M | Face | Slight redness | Completely cleared spots I used it on |
| SP | 7 | 60% | M | Scalp | — | Prevents carcinomas from forming |
| TF | 7 | 50% | M | Chest | — | — |
| WD | 5 | 40% | M | Face | — | — |
| Average | 7.2 | 64.5% | — | — | — | |

[1]response is the physician's evaluation of overall response of the AK's with 10 being a great response and 0 being no response
[2]the percentage of AK's being treated that cleared completely.

Figure 1:
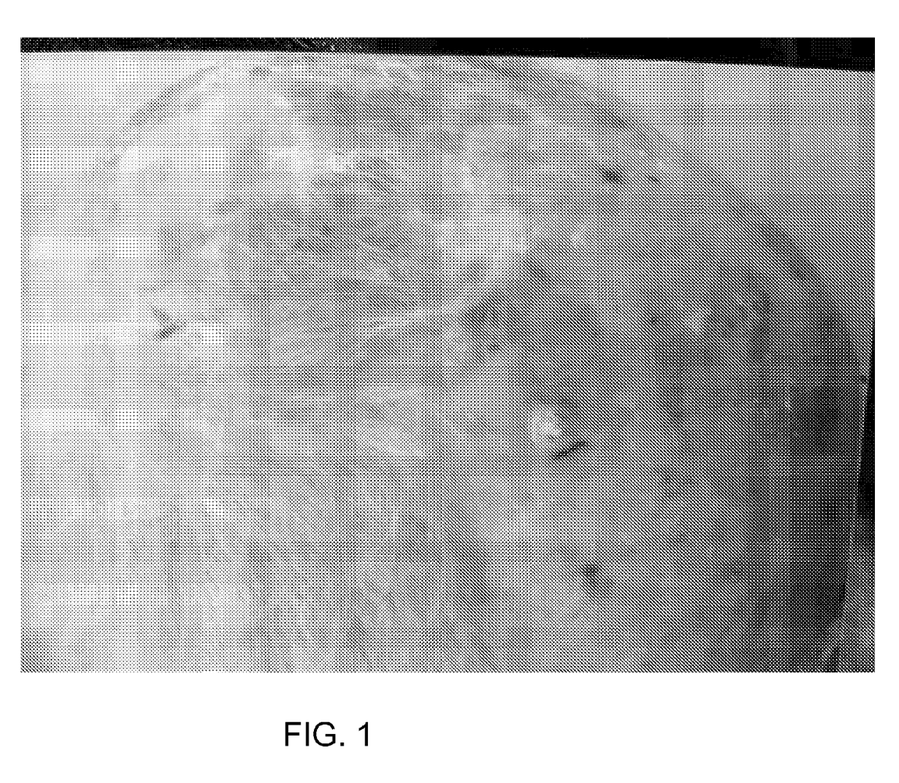
FIG. 1 is a photograph of the scalp of Patient 1 showing AKs prior to treatment.
Figure 2:
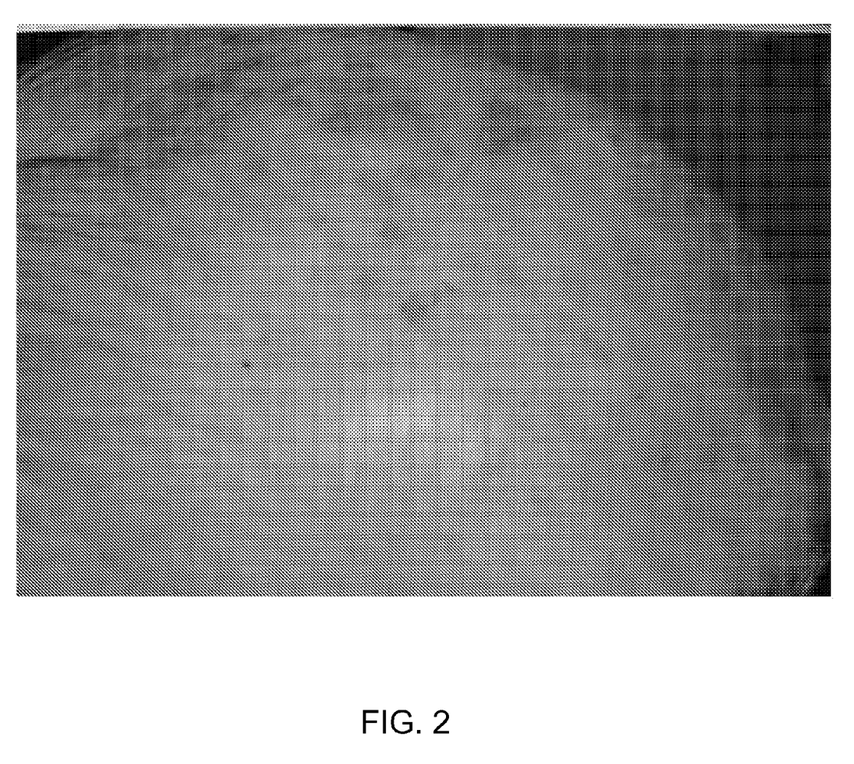
FIG. 2 is a photograph of the scalp of Patient 1 following treatment according the present invention.
Figure 3:
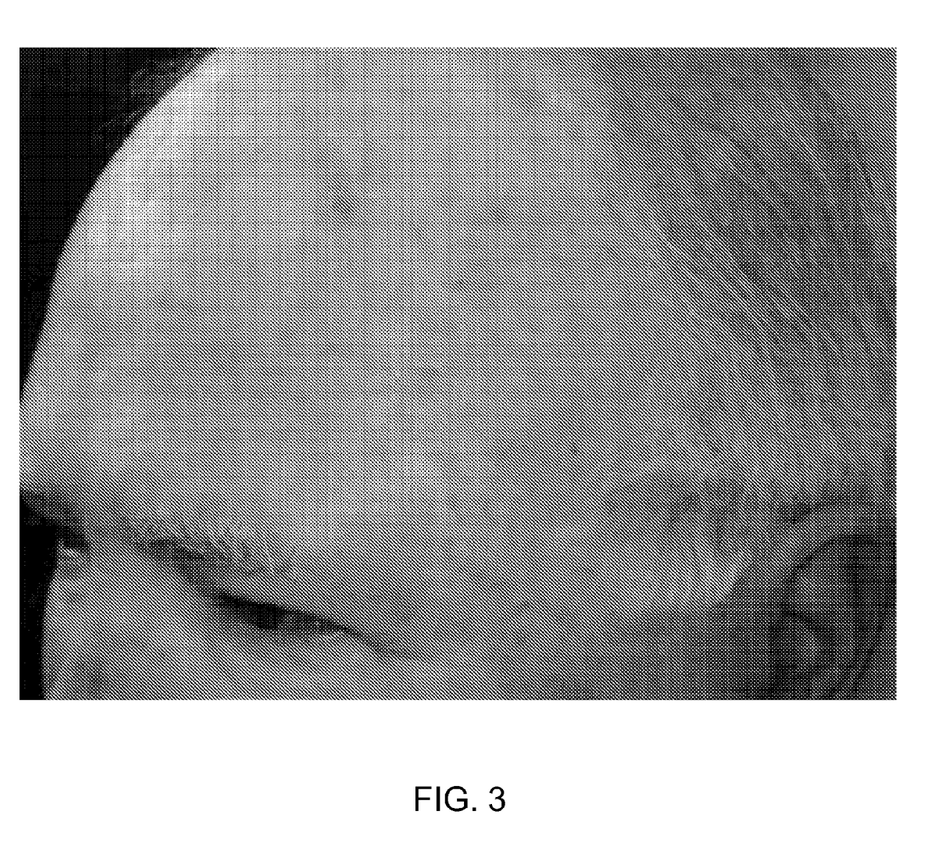
FIG. 3 is a photograph of the scalp of Patient 2 showing AKs prior to treatment.
Figure 4:
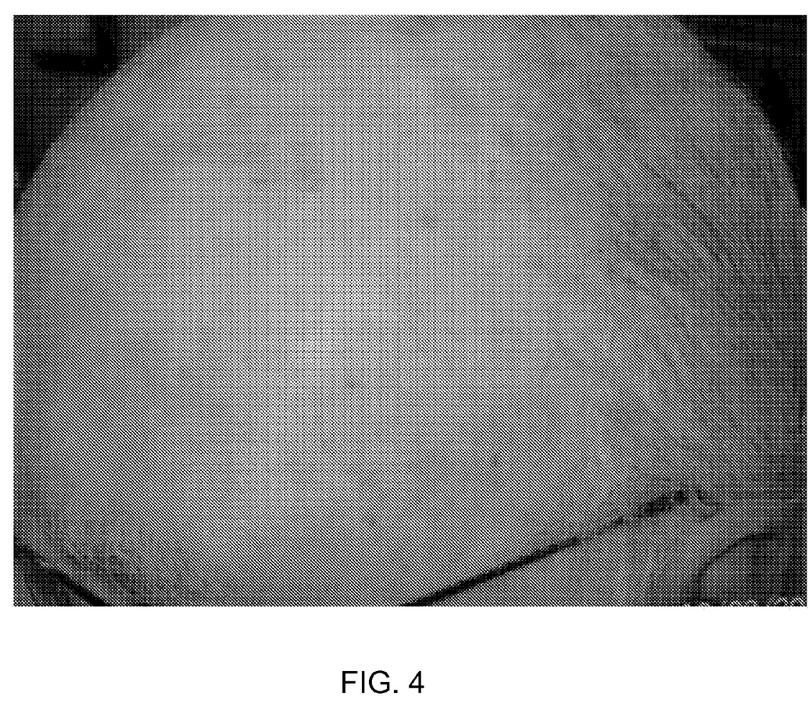
FIG. 4 is a photograph of the scalp of Patient 2 following treatment according the present invention.
Figure 5:
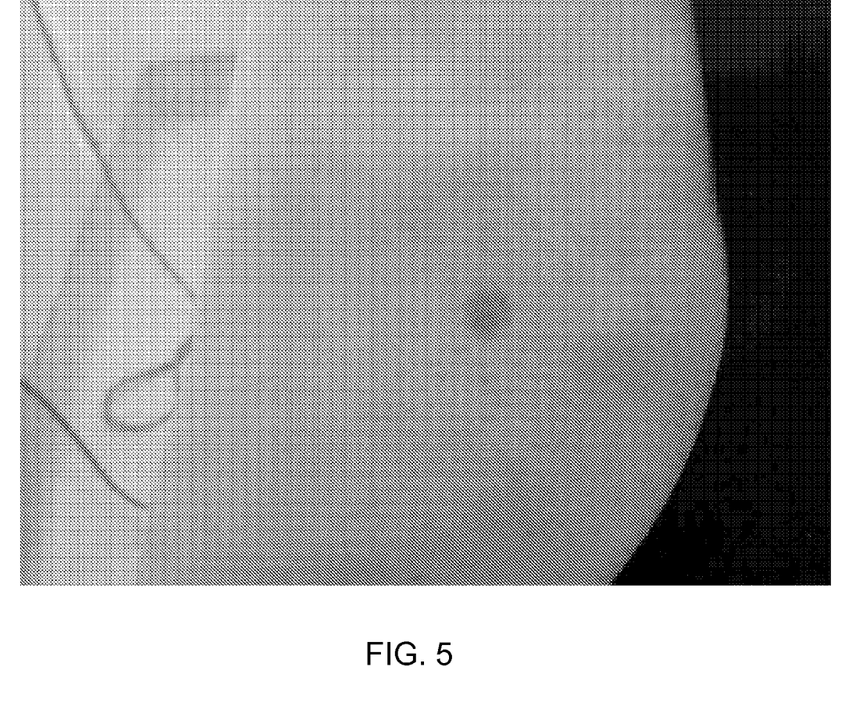
FIG. 5 is a photograph of the leg of Patient 3 showing an AK prior to treatment.
Figure 6:
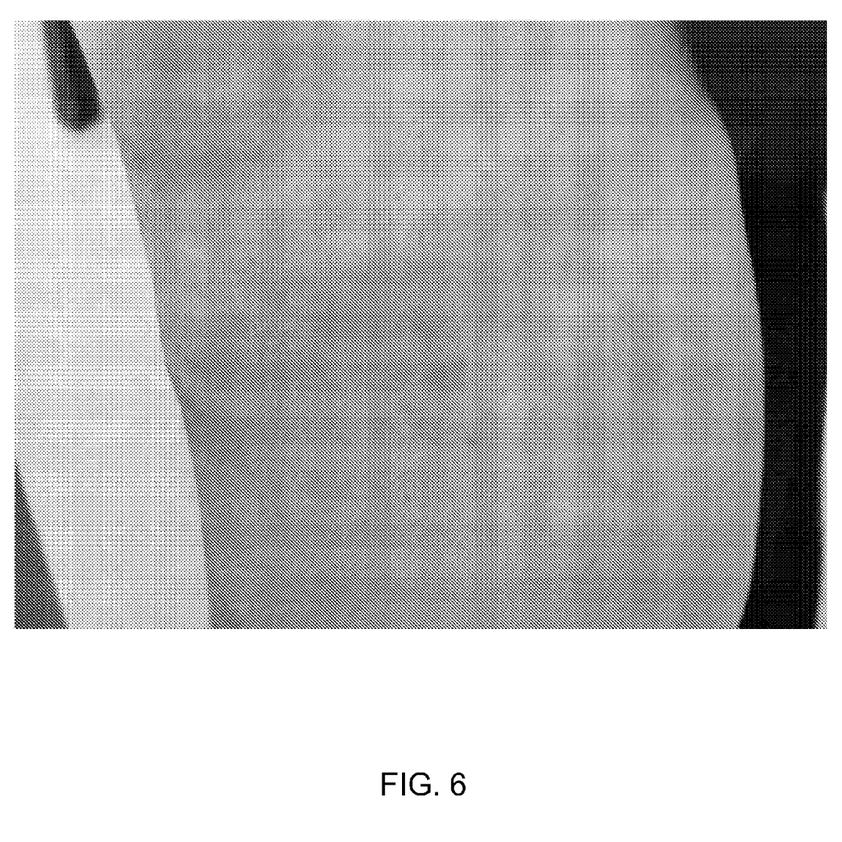
FIG. 6 is a photograph of the leg of Patient 3 following treatment according the present invention.

FIG. 1 shows the scalp of Patient 1 prior to treatment with the 0.3% gentamicin/0.2% colchicine cream. This should be contrasted with FIG. 2 which shows the same scalp after the treatment. Similarly, FIG. 3 shows the scalp of Patient 2 prior to treatment, and FIG. 4 shows the scalp of Patient 2 after treatment. FIG. 5 shows a lesion on the leg of Patient 3 pretreatment while FIG. 6 shows the same leg after the treatment. The primary lesions cleared completely or almost completely. In addition, the overall appearance of the skin improved.

CONCLUSIONS

The 0.3% gentamicin with 0.2% colchicine was somewhat more effective than our preliminary results with related compositions. Because the final study included a number of recalcitrant patients who had failed LN$_2$ treatments, it is likely that this composition is even more effective than the comparative results might suggest.

From this final study we were able to conclude:

1. The 0.3% gentamicin with 0.2% colchicine cream was effective at clearing difficult AKs.

2. For the patients who were constantly developing skin carcinomas, that is, SCC and BCC, there appeared to be a decreased incidence in the development of additional carcinomas.

3. Although we did not monitor all reactions, patients reported much less reaction of redness, scrabbling, pain, and ulceration compared to other products such as Efudex® (brand of fluorouracil cream), Carac® (brand of fluorouracil cream) or Aldara® (brand of imiquimod cream). We confirmed this from the reactions we monitored and by comparing results from the patients who had been treated with the other products.

4. The inventive cream worked much better than Solaraze® (brand of diclofenac gel) in abolishing AKs. We found that Solaraze® was generally not effective at clearing AK's and was effective only in controlling some of the growth of AKs.

5. Therefore, this composition is more effective than competing products while causing less irritation and pain.

Our study demonstrates that the AKs are effectively treated with the new combination and separately using gentamicin by itself. This is an entirely new use of gentamicin. It would appear that gentamicin treatment results in the normalization of some genetic mutations. Other aminoglycosides with effects on m-RNA translation are likely to show similar efficacy. Colchicine would be expected to slow cell division by inhibiting spindle formation perhaps thereby allowing more time for a suboptimal cellular repair system to operate. Other tubulin-binding compounds would be expected to show similar results. Significantly, the combination of gentamicin with colchicine is more effective than either of these agents alone. Because gentamicin seems to reduce the level of irritation caused by colchicine, it was possible in the presence of gentamicin to effectively use a higher concentration of colchicine. As an alternative to every other day application of the combined cream, it is also possible to alternate daily application of the combination with application of gentamicin alone as a means of further reducing irritation.

It will be appreciated that other aminoglycoside antibiotics show significant effects on nonsense mutations. The present invention includes the use of any of these aminoglycosides. Also, one of ordinary skill in the art will readily appreciate that colchicine is not the only tubulin binding drug. The present invention necessary includes combination of aminoglycoside antibiotics with such tubulin binding drugs.

The following claims are to be understood to include what is specifically illustrated and described above, what is conceptually equivalent, what can be obviously substituted and also what incorporates the essential idea of the invention. The illustrated embodiment has been set forth only for the purposes of example and that should not be taken as limiting the invention. Those skilled in the art will appreciate that various adaptations and modifications of the just-described preferred embodiment can be configured without departing from the scope of the invention. Therefore, it is to be understood that, within the scope of the appended claims, the invention may be practiced other than as specifically described herein.

What is claimed is:

1. A composition for the topical treatment of actinic keratoses comprising between 0.1% by weight and 1.0% by weight gentamicin and between 0.1% by weight and 1.0% by weight colchicine in a pharmaceutically acceptable cream base composition.

2. The composition according to claim 1 comprising about 1.0% by weight gentamicin and about 0.1% by weight colchicine.

3. The composition according to claim 1 comprising about 0.3% by weight gentamicin and about 0.2% by weight colchicine.

4. A method for treatment of actinic keratoses comprising the step of periodically topically applying an aminoglycoside antibiotic in a pharmaceutically acceptable cream base composition to actinic keratoses.

5. The method according to claim 4, wherein the aminoglycoside antibiotic is gentamicin.

6. The method according to claim 4, wherein a drug that binds to tubulin is added to said composition.

7. The method according to claim 6, wherein application of the composition of an aminoglycoside antibiotic and a tubulin binding drug is alternated with the composition containing only aminoglycoside antibiotic.

8. The method according to claim 6, wherein the drug that binds to tubulin is colchicine.

9. The method according to claim 8, wherein the composition comprises between 0.1% by weight and 1.0% by weight gentamicin and between 0.1% by weight and 1.0% by weight colchicine.

10. The method according to claim 9, wherein the composition comprises 1.0% by weight gentamicin and 0.1% by weight colchicine.

11. The method according to claim 9, wherein the composition comprises about 0.3% by weight gentamicin and about 0.2% by weight colchicine.

* * * * *